(12) United States Patent
Hundorf et al.

(10) Patent No.: US 8,552,252 B2
(45) Date of Patent: Oct. 8, 2013

(54) DISPOSABLE ABSORBENT ARTICLE WITH ENHANCED ABSORPTION PROPERTIES

(76) Inventors: Harald Hermann Hundorf, Bonn (DE); Holger Beruda, Schwalbach (DE); Horst Blessing, Cincinnati, OH (US); Peter Dziezok, Hochheim (DE); Axel Krause, Erftsadt (DE); Mattias Schmidt, Idstein (DE); Lutz Stelzig, Frankfurt am Main (DE)

( * ) Notice: Subject to any disclaimer, the term of this patent is extended or adjusted under 35 U.S.C. 154(b) by 0 days.

(21) Appl. No.: 13/197,893

(22) Filed: Aug. 4, 2011

(65) Prior Publication Data

US 2011/0288513 A1    Nov. 24, 2011

Related U.S. Application Data

(62) Division of application No. 12/141,143, filed on Jun. 18, 2008, now Pat. No. 8,017,827.

(60) Provisional application No. 60/936,146, filed on Jun. 18, 2007.

(51) Int. Cl.
*A61F 13/15* (2006.01)

(52) U.S. Cl.
USPC ........... 604/367; 604/368; 604/372; 604/370; 604/385.101; 604/378

(58) Field of Classification Search
USPC ........... 604/367, 368, 372, 370, 378, 385.101
See application file for complete search history.

(56) References Cited

U.S. PATENT DOCUMENTS

| | | |
|---|---|---|
| 3,670,731 A | 6/1972 | Harmon |
| 3,848,594 A | 11/1974 | Buell |
| 3,860,003 A | 1/1975 | Buell |
| 4,055,180 A | 10/1977 | Karami |
| 4,259,220 A | 3/1981 | Bunnelle et al. |
| 4,381,783 A | 5/1983 | Elias |
| 4,469,710 A | 9/1984 | Bielley et al. |
| 4,515,595 A | 5/1985 | Kievie et al. |
| 4,596,568 A | 6/1986 | Flug |
| 4,610,678 A | 9/1986 | Weisman et al. |
| 4,662,875 A | 5/1987 | Hirotsu et al. |
| 4,670,011 A | 6/1987 | Mesek |
| 4,695,278 A | 9/1987 | Lawson |
| 4,704,115 A | 11/1987 | Buell |
| RE32,649 E | 4/1988 | Brandt et al. |
| 4,834,735 A | 5/1989 | Alemany et al. |
| 4,848,815 A | 7/1989 | Molloy |
| 4,869,724 A | 9/1989 | Scripps |
| 4,888,231 A | 12/1989 | Angstadt |
| 4,909,803 A | 3/1990 | Aziz et al. |
| 4,940,464 A | 7/1990 | Van Gompel et al. |
| 4,960,477 A | 10/1990 | Mesek |
| 4,994,053 A | 2/1991 | Lang |
| 5,032,120 A | 7/1991 | Freeland et al. |

(Continued)

FOREIGN PATENT DOCUMENTS

| | | |
|---|---|---|
| EP | 0 149 880 A2 | 7/1985 |
| EP | 0 203 289 A2 | 12/1986 |

(Continued)

*Primary Examiner* — Jacqeline F. Stephens

(74) *Attorney, Agent, or Firm* — Laura L. Whitmer; Thibault Fayette

(57) ABSTRACT

A substantially cellulose free absorbent core comprising absorbent polymer material having a saline flow conductivity greater than about $100 \times 10^{-7}$ cm$^3$•sec/g and a centrifuge retention capacity of greater than about 20 g/g. A disposable absorbent article is also disclosed.

20 Claims, 16 Drawing Sheets

(56) References Cited

U.S. PATENT DOCUMENTS

| | | |
|---|---|---|
| 5,037,416 A | 8/1991 | Allen et al. |
| 5,087,255 A | 2/1992 | Sims et al. |
| 5,092,861 A | 3/1992 | Nomura et al. |
| 5,124,188 A | 6/1992 | Roe et al. |
| 5,137,537 A | 8/1992 | Herron et al. |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,242,436 A | 9/1993 | Weil et al. |
| 5,246,433 A | 9/1993 | Hasse et al. |
| 5,260,345 A | 11/1993 | DesMarais et al. |
| 5,269,775 A | 12/1993 | Freeland et al. |
| 5,387,207 A | 2/1995 | Dyer et al. |
| 5,397,316 A | 3/1995 | LaVon et al. |
| 5,401,792 A | 3/1995 | Babu et al. |
| 5,411,497 A | 5/1995 | Tanzer et al. |
| 5,425,725 A | 6/1995 | Tanzer et al. |
| 5,460,622 A | 10/1995 | Dragoo et al. |
| 5,518,801 A | 5/1996 | Chappell et al. |
| 5,527,300 A | 6/1996 | Sauer |
| 5,554,145 A | 9/1996 | Roe et al. |
| 5,562,646 A | 10/1996 | Goldman et al. |
| 5,569,234 A | 10/1996 | Buell et al. |
| 5,571,096 A | 11/1996 | Dobrin et al. |
| 5,591,155 A | 1/1997 | Nishikawa et al. |
| 5,599,335 A | 2/1997 | Goldman et al. |
| 5,625,222 A | 4/1997 | Yoneda et al. |
| 5,628,741 A | 5/1997 | Buell et al. |
| 5,658,268 A | 8/1997 | Johns et al. |
| 5,762,641 A | 6/1998 | Bewick-Sonntag et al. |
| 5,788,684 A | 8/1998 | Abuto et al. |
| 5,833,678 A | 11/1998 | Ashton et al. |
| 5,897,545 A | 4/1999 | Kline et al. |
| 5,944,706 A | 8/1999 | Palumbo et al. |
| 5,957,908 A | 9/1999 | Kline et al. |
| 6,004,306 A | 12/1999 | Robles et al. |
| 6,090,994 A | 7/2000 | Chen |
| 6,120,487 A | 9/2000 | Ashton |
| 6,120,489 A | 9/2000 | Johnson et al. |
| 6,132,411 A | 10/2000 | Huber et al. |
| 6,231,556 B1 | 5/2001 | Osborn, III |
| 6,258,996 B1 | 7/2001 | Goldman |
| 6,368,687 B1 | 4/2002 | Joseph et al. |
| 6,376,034 B1 | 4/2002 | Brander |
| 6,383,431 B1 | 5/2002 | Dobrin et al. |
| 6,414,214 B1 | 7/2002 | Engelhardt et al. |
| 6,429,350 B1 | 8/2002 | Tanzer et al. |
| 6,458,877 B1 | 10/2002 | Ahmed et al. |
| 6,645,569 B2 | 11/2003 | Cramer et al. |
| 6,863,933 B2 | 3/2005 | Cramer et al. |
| 6,972,011 B2 | 12/2005 | Maeda et al. |
| 7,108,916 B2 | 9/2006 | Ehrnsperger et al. |
| 7,112,621 B2 | 9/2006 | Rohrbaugh et al. |
| 2002/0007169 A1 | 1/2002 | Graef et al. |
| 2002/0102392 A1 | 8/2002 | Fish et al. |
| 2002/0115969 A1 | 8/2002 | Maeda et al. |
| 2002/0151634 A1 | 10/2002 | Rohrbaugh et al. |
| 2002/0192366 A1 | 12/2002 | Cramer et al. |
| 2003/0105190 A1 | 6/2003 | Diehl et al. |
| 2003/0148684 A1 | 8/2003 | Cramer et al. |
| 2003/0233082 A1 | 12/2003 | Kline et al. |
| 2004/0097895 A1 | 5/2004 | Busam et al. |
| 2004/0158212 A1 | 8/2004 | Ponomarenko et al. |
| 2004/0162536 A1 | 8/2004 | Becker et al. |
| 2004/0167486 A1 | 8/2004 | Busam |
| 2005/0008839 A1 | 1/2005 | Cramer et al. |
| 2005/0159720 A1 | 7/2005 | Gentilcore et al. |
| 2006/0177647 A1 | 8/2006 | Schmidt et al. |
| 2006/0240229 A1 | 10/2006 | Ehrnsperger et al. |
| 2007/0043330 A1 | 2/2007 | Lankhof et al. |
| 2007/0088308 A1 | 4/2007 | Ehrnsperger et al. |
| 2007/0118087 A1 | 5/2007 | Flohr et al. |
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0219521 A1 | 9/2007 | Hird et al. |
| 2008/0312623 A1 | 12/2008 | Hundorf et al. |

FOREIGN PATENT DOCUMENTS

| | | |
|---|---|---|
| EP | 0 640 330 A1 | 3/1995 |
| EP | 1 088 537 A2 | 4/2001 |
| EP | 1621167 | 2/2006 |
| JP | 06-269475 | 9/1994 |
| JP | 2002-113800 | 4/2002 |
| JP | 2002-325799 | 11/2002 |
| WO | WO 95/16746 A1 | 6/1995 |
| WO | WO 97/11659 | 4/1997 |
| WO | WO 01/15647 A1 | 3/2001 |
| WO | WO 02/064877 A2 | 8/2002 |
| WO | WO 2004/071539 A2 | 8/2004 |
| WO | WO 2006/062258 A2 | 6/2006 |

DISPOSABLE ABSORBENT ARTICLE WITH ENHANCED ABSORPTION PROPERTIES

CROSS REFERENCE TO RELATED APPLICATIONS

This application is a divisional of U.S. application Ser. No. 12/141,143, filed on Jun. 18, 2008 now U.S. Pat. No. 8,017,827, which claims the benefit of U.S. Provisional Application No. 60/936,146, filed on Jun. 18, 2007.

FIELD OF THE INVENTION

The present invention generally relates to an absorbent article, and more particularly to a disposable absorbent article, such as a diaper, with enhanced absorption properties.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Some absorbent articles, like diapers, contain an absorbent polymer material (also known as super absorbent polymer). Absorbent polymer material absorbs liquid and swells. Absorbent articles may be made relatively thin and flexible when made with absorbent polymer material and thin and flexible absorbent articles may fit better and more comfortably and may be more neatly and conveniently packaged and stored. Generally, the more effective the absorbent particulate polymer material is as an absorbent, the thinner and more flexible the absorbent article containing the absorbent particulate polymer material can be.

Thus, there remains a need for even more effective absorbent polymer material and even more thin and flexible absorbent articles.

SUMMARY OF THE INVENTION

The present invention addresses one or more technical problems described above and provides a disposable absorbent article which may comprise a chassis and a substantially cellulose free absorbent core located between the topsheet and the backsheet and including absorbent polymer material, wherein the absorbent particulate polymer material has a saline flow conductivity greater than about $100 \times 10^{-7}$ $cm^3 \cdot sec/g$ and a centrifuge retention capacity of greater than about 20 g/g.

According to another aspect of this invention, an absorbent core as described herein above is provided.

Other features and advantages of the invention may be apparent from reading the following detailed description, drawings, and claims.

DETAILED DESCRIPTION OF THE INVENTION

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
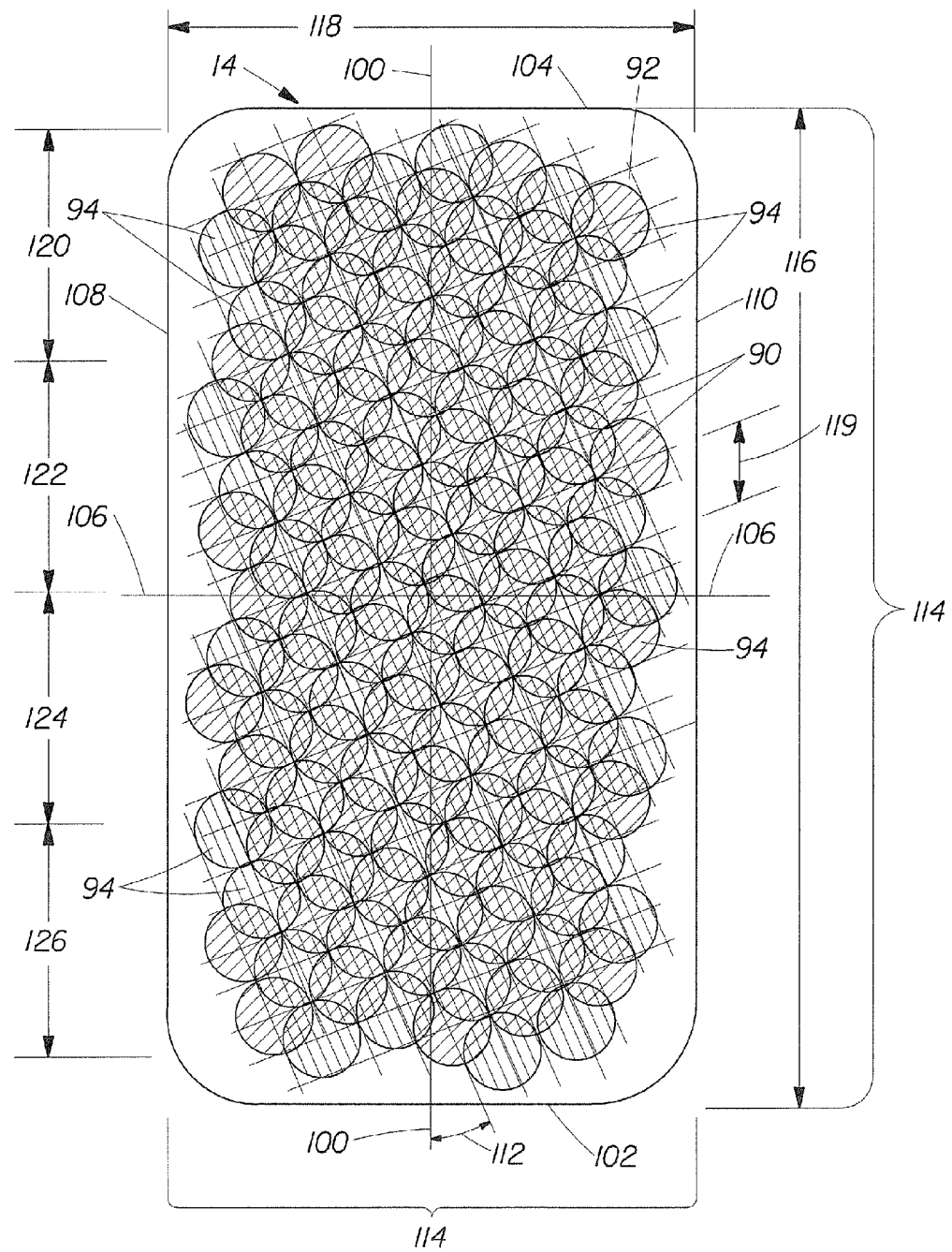
FIG. 8 is a plan view of the absorbent core illustrated in FIGS. 7a and 7b.

"Absorbent particulate polymer material area" as used herein refers to the area of the core wherein the first substrate 64 and second substrate 72 are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate 64 and second substrate 72.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

Figure 1:
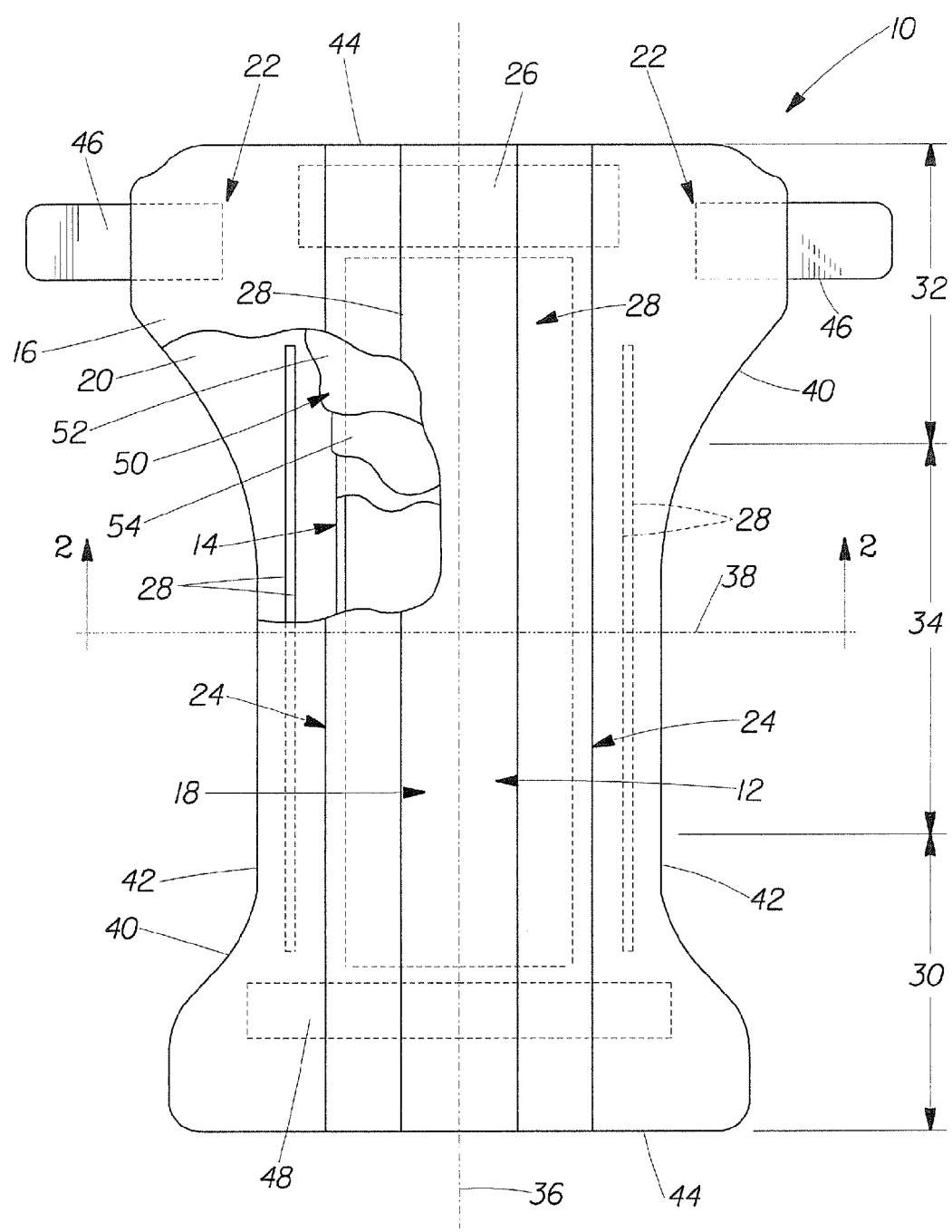
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Figure 2:
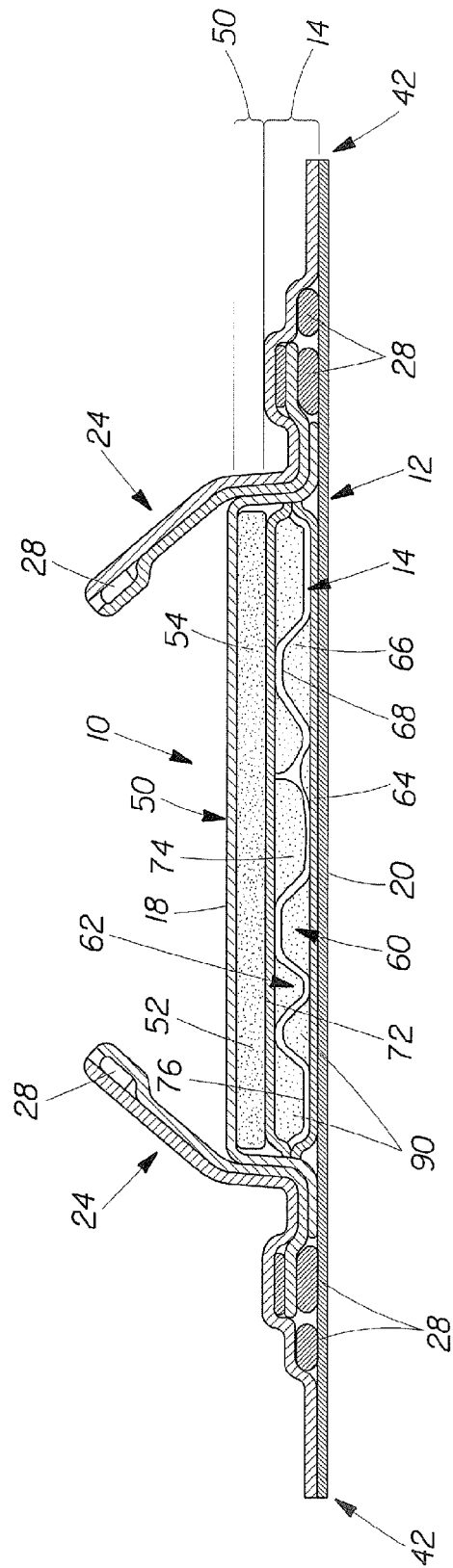
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. According to a certain embodiment, diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a non-woven, which may be hydrophilic. Further, according to a certain embodiment, one or both of the upper and lower acquisition layers 52 and 54 may comprise the chemically cross-linked cellulosic fibers, which may or may not form part of a non-woven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to another embodiment, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

A relevant attribute of the upper acquisition layer 54 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. Without wishing to be bound by theory, a given distribution material may have a definable capillary suction. The ability of the lower acquisition layer 54 to move liquid vertically via capillary forces will be directly impacted by gravity and the opposing capillary forces associated with desorption of the upper acquisition layer. Minimizing these capillary forces may positively impact the performance of the lower acquisition layer 54. However, in a certain embodiment the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, in a certain embodiment, the lower acquisition layer 54 may have a minimum MDP of greater than 5 cm. Further, according to exemplary embodiments, the lower acquisition layer 54 has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. patent application Ser. No. 11/600,691 (Flohr et al.). For example, according to a first embodiment, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated non-woven is that disclosed in the co-pending patent application Ser. No. 10/758, 066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
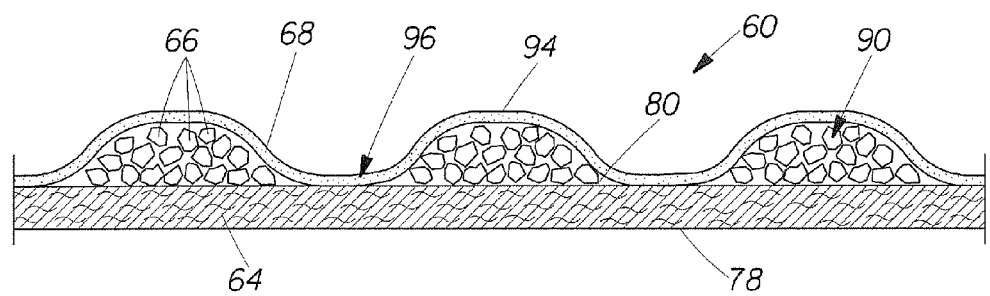
FIG. 3 is a partial cross sectional view of an absorbent core layer in accordance with an embodiment of this invention.

The absorbent core 14 in FIGS. 1-8 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

Likewise, as best illustrated in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. Likewise, the substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
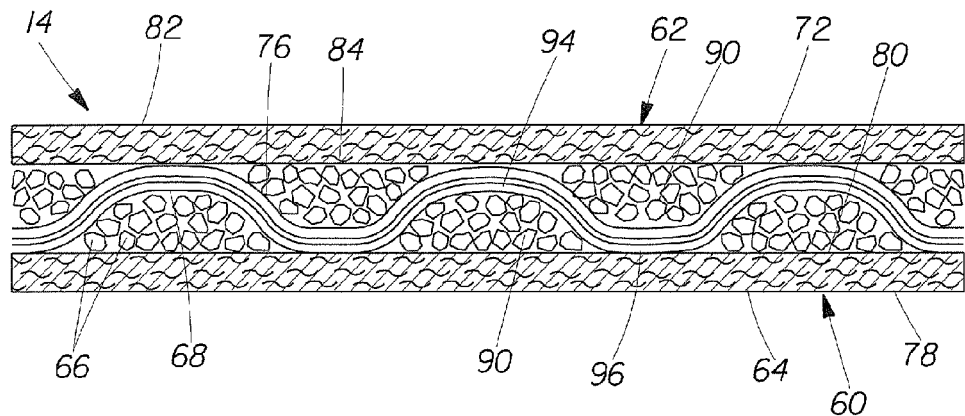
FIG. 7a is a partial sectional view of an absorbent core comprising a combination of the first and second absorbent core layers illustrated in FIGS. 5 and 6.
Figure 7B:
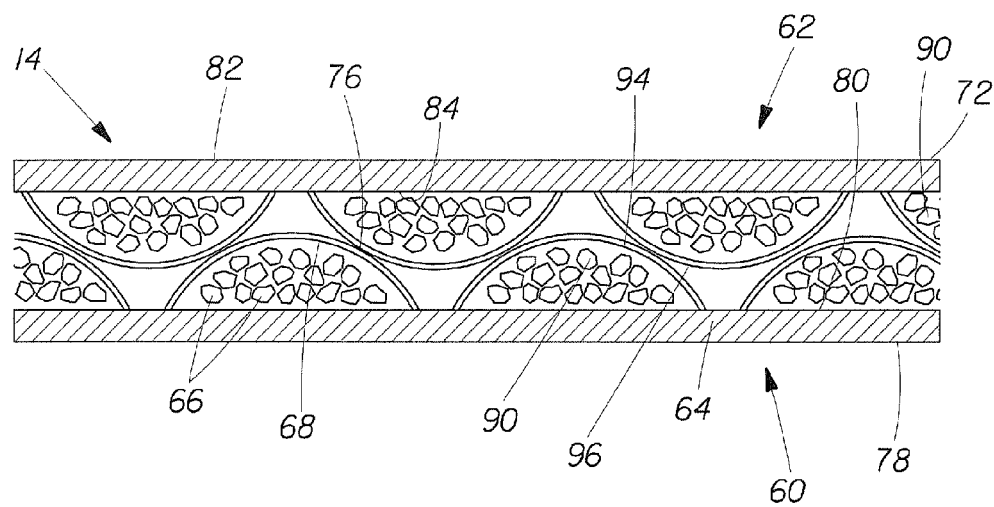
FIG. 7b is a partial sectional view of an absorbent core comprising a combination of the first and second absorbent core layers illustrated in FIGS. 5 and 6

As best seen in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In a certain embodiment as illustrated in FIG. 8, the amount of absorbent particulate polymer material 66 and 74 may vary along the length 116 of the grid pattern 92. In a certain embodiment, the grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

According to an embodiment, a suitable absorbent particulate polymer material 66 and 74, even in the swollen state, i.e., when liquid has been absorbed, does not substantially obstruct the liquid flow throughout the material, especially when the material has a permeability, as expressed by the saline flow conductivity of the absorbent polymer material, of greater than about 10, 40, 80, 100, 110, 120, 150, or $200 \times 10^{-7}$ cm$^3 \cdot$sec/g and a centrifuge retention capacity (CRC) of greater than about 20 g/g, greater than about 25 g/g, or less than about 40 g/g, less than about 35 g/g. In one embodiment of the present invention, the absorbent particulate polymer material has a saline flow conductivity greater than about $100 \times 10^{-7}$ cm$^3 \cdot$sec/g and a centrifuge retention capacity of greater than about 20 g/g. In another embodiment of the invention, the absorbent particulate polymer material has a saline flow conductivity greater than about $70 \times 10^{-7}$ cm$^3 \cdot$sec/g and a centrifuge retention capacity of greater than about 25 g/g. Saline flow conductivity is a parameter well recognized in the art and is to be measured in accordance with the test disclosed in U.S. patent application Ser. No. 11/724,341 filed on Mar. 15, 2007. Centrifuge retention capacity is another parameter well recognized in the art and is to be measured in accordance with the test disclosed hereinbelow. According to a certain embodiment, the absorbent polymer material has an Absorption Against Pressure (AAP) of at least about 20 g/g, greater than about 23 g/g, or greater than about 25 g/g as measured according to the test described below. Absorbent polymer materials for use in certain embodiments have a basis weight of at least about 200 g/m$^2$, at least about 400 g/m$^2$, or at least about 600 g/m$^2$. To maintain flexibility the basis weight is desirably less than about 2000 g/m$^2$.

In certain embodiments wherein the absorbent core 14 is substantially cellulose free, the absorbent core 14 has a density greater than about 0.4 g/m$^3$, greater than about 0.5 g/m$^3$, or greater than about 0.6 g/m$^3$.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

Figure 4:
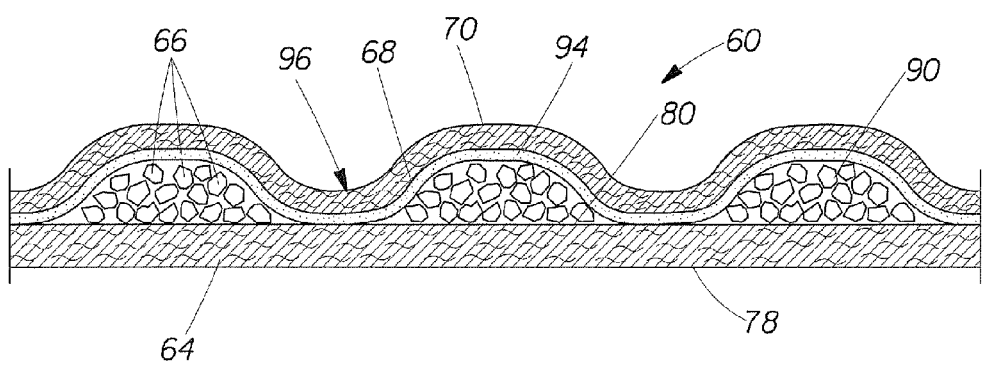
FIG. 4 is a partial cross sectional view of an absorbent core layer in accordance with another embodiment of this invention.

The thermoplastic adhesive material 68 and 76 may serve to cover and at least partially immobilize the absorbent particulate polymer material 66 and 74. In one embodiment of the present invention, the thermoplastic adhesive material 68 and 76 can be disposed essentially uniformly within the absorbent particulate polymer material 66 and 74, between the polymers. However, in a certain embodiment, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet, such that the absorbent core 14 achieves an absorbent particulate polymer material loss of no more than about 70%, 60%, 50%, 40%, 30%, 20%, 10% according to the Wet Immobilization Test described herein. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

Without wishing to be bound by theory, it has been found that those thermoplastic adhesive materials which are most useful for immobilizing the absorbent particulate polymer material 66 and 74 combine good cohesion and good adhesion behavior. Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 absorbs liquid, the absorbent particulate polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent particulate polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other non-woven layer, such layers may be pre-treated with an auxiliary adhesive.

In certain embodiments, the thermoplastic adhesive material 68 and 76 will meet at least one, or several, or all of the following parameters:

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

Figure 9:
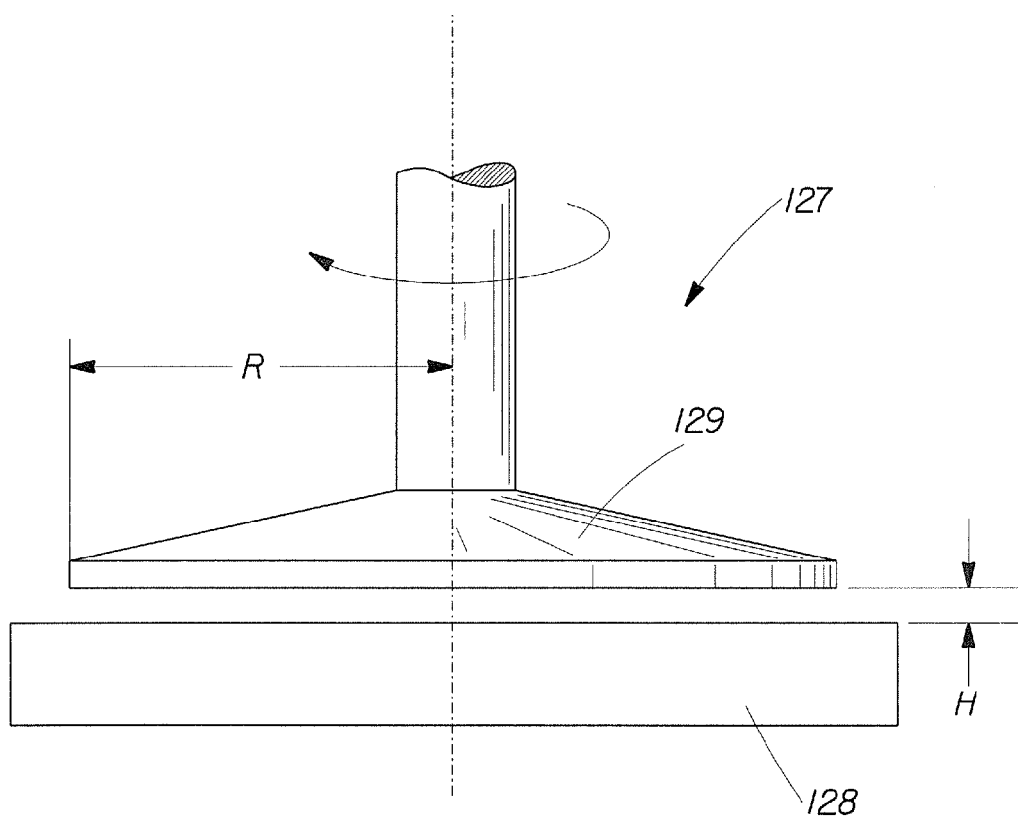
FIG. 9 is a schematic representation of a rheometer.

G' is measured using a rheometer as schematically shown in FIG. 9 for the purpose of general illustration only. The rheometer 127 is capable of applying a shear stress to the adhesive and measuring the resulting strain (shear deformation) response at constant temperature. The adhesive is placed between a Peltier-element acting as lower, fixed plate 128 and an upper plate 129 with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H. B. Fuller Co. (St. Paul, Minn.) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72.

Figure 10:
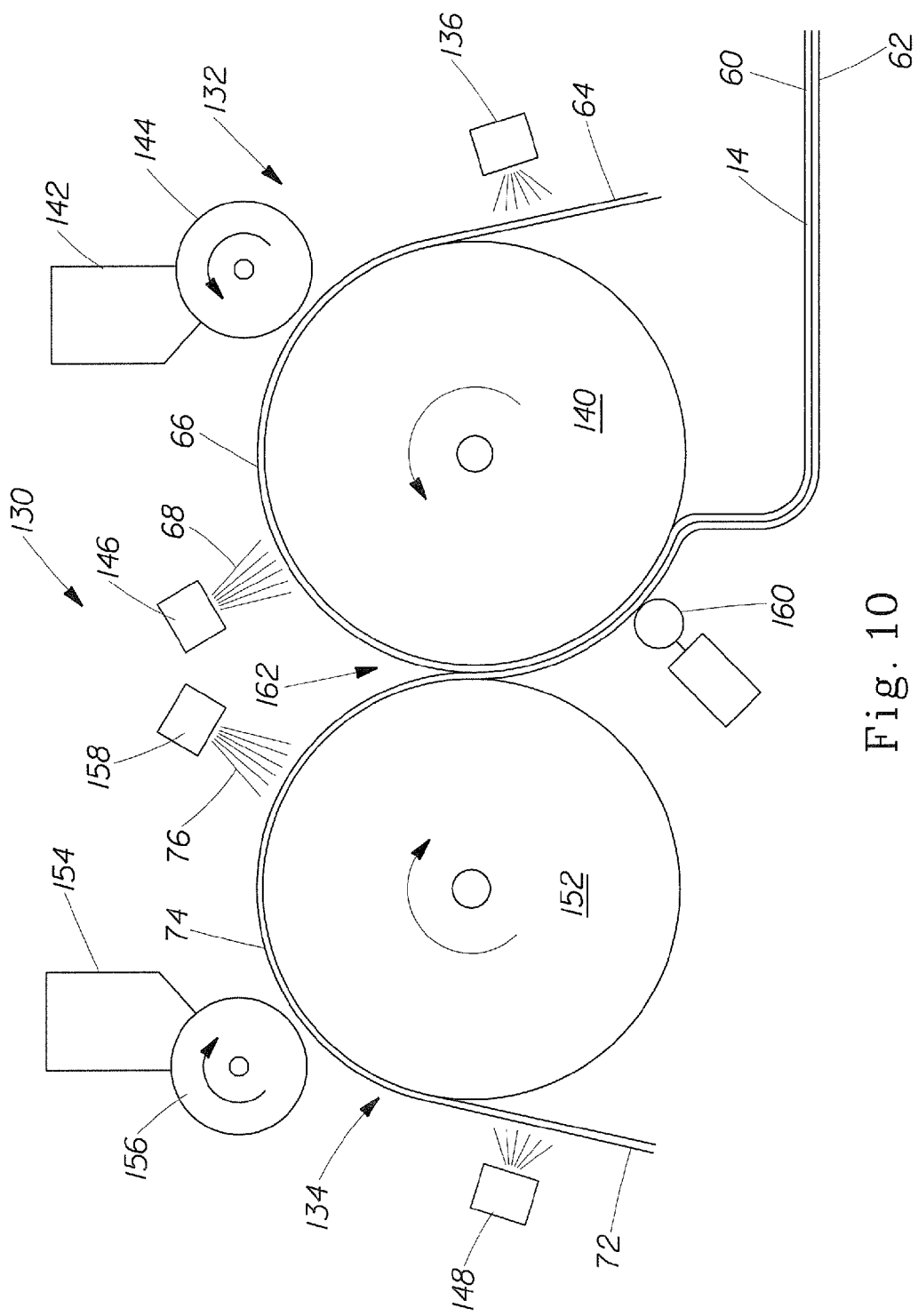
FIG. 10 is a schematic illustration of a process for making an absorbent core in accordance with an embodiment of this invention.

A printing system 130 for making an absorbent core 14 in accordance with an embodiment of this invention is illustrated in FIG. 10 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic adhesive material applicator 146 for applying the thermoplastic adhesive material 68 to the substrate 64 and the absorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 11:
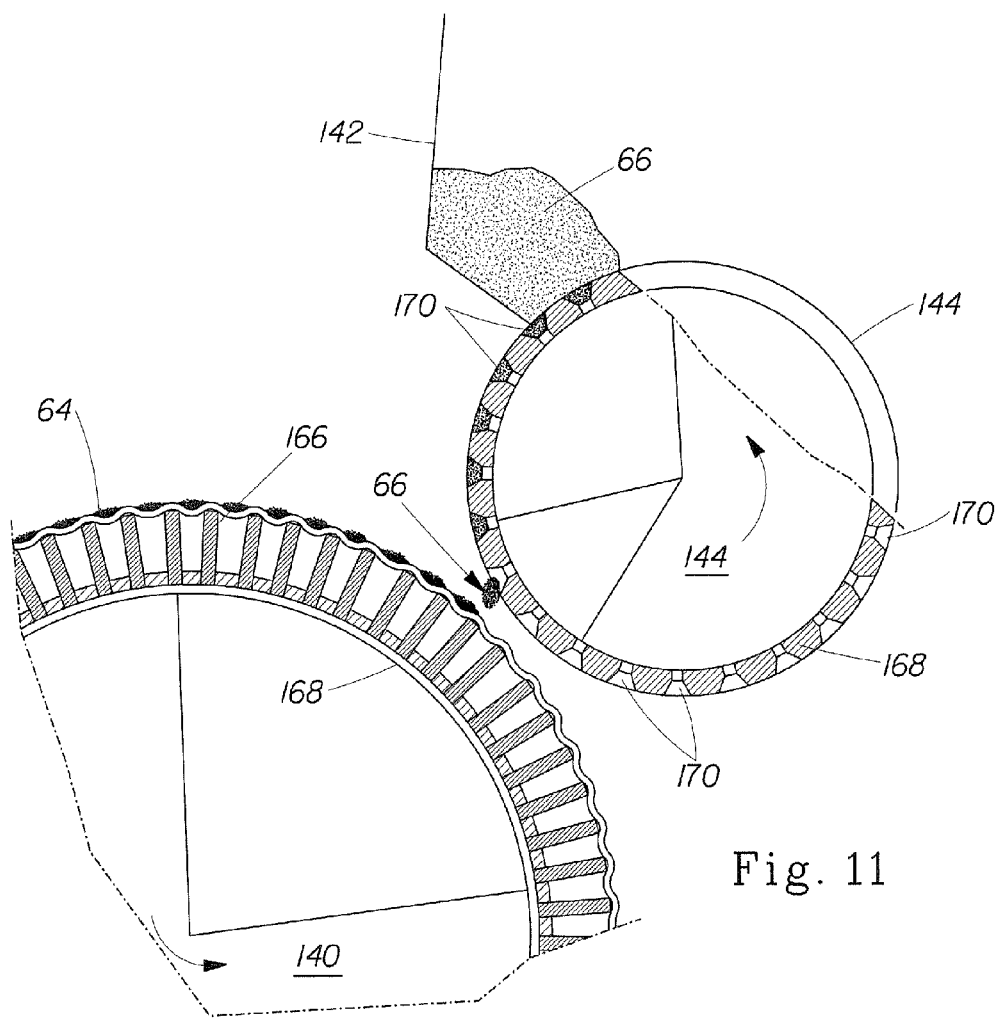
FIG. 11 is a partial sectional view of an apparatus for making an absorbent core in accordance with an embodiment of this invention.
Figure 14:
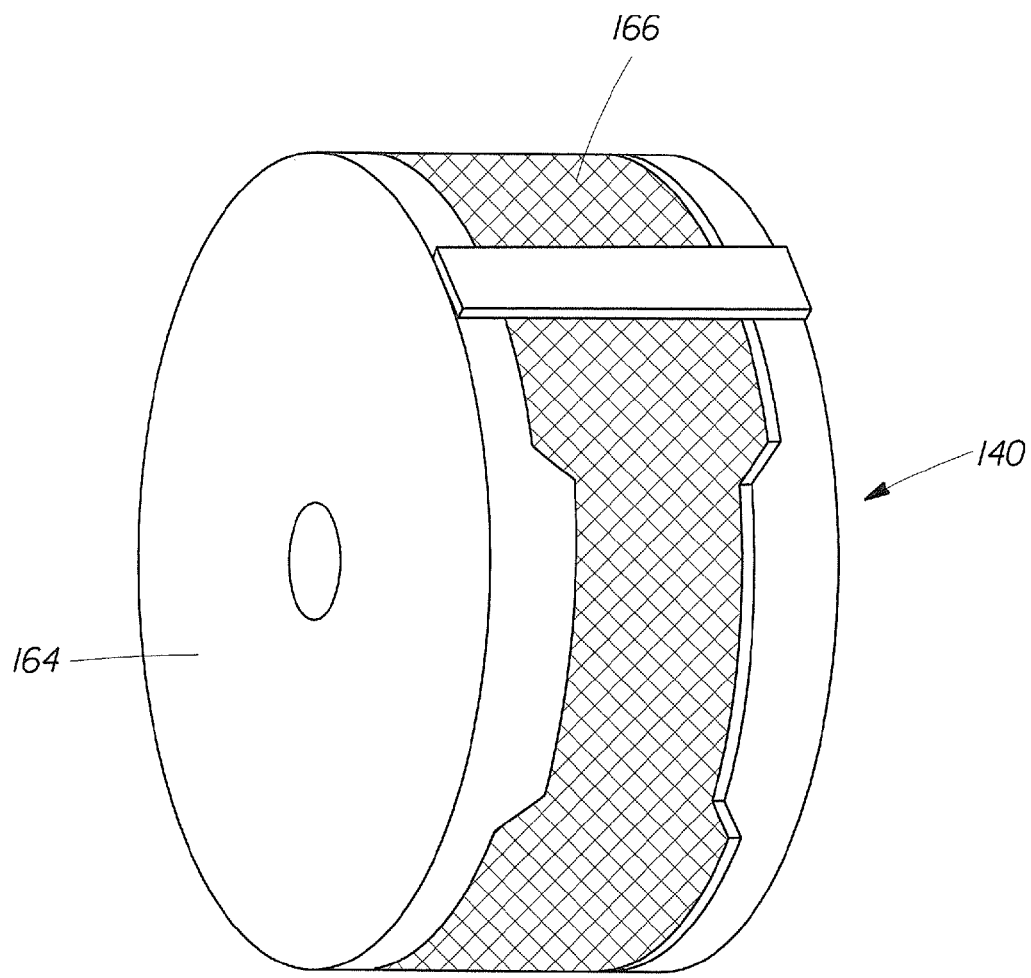
FIG. 14 is a perspective view of the supporting roll illustrated in FIG. 12.
Figure 15:
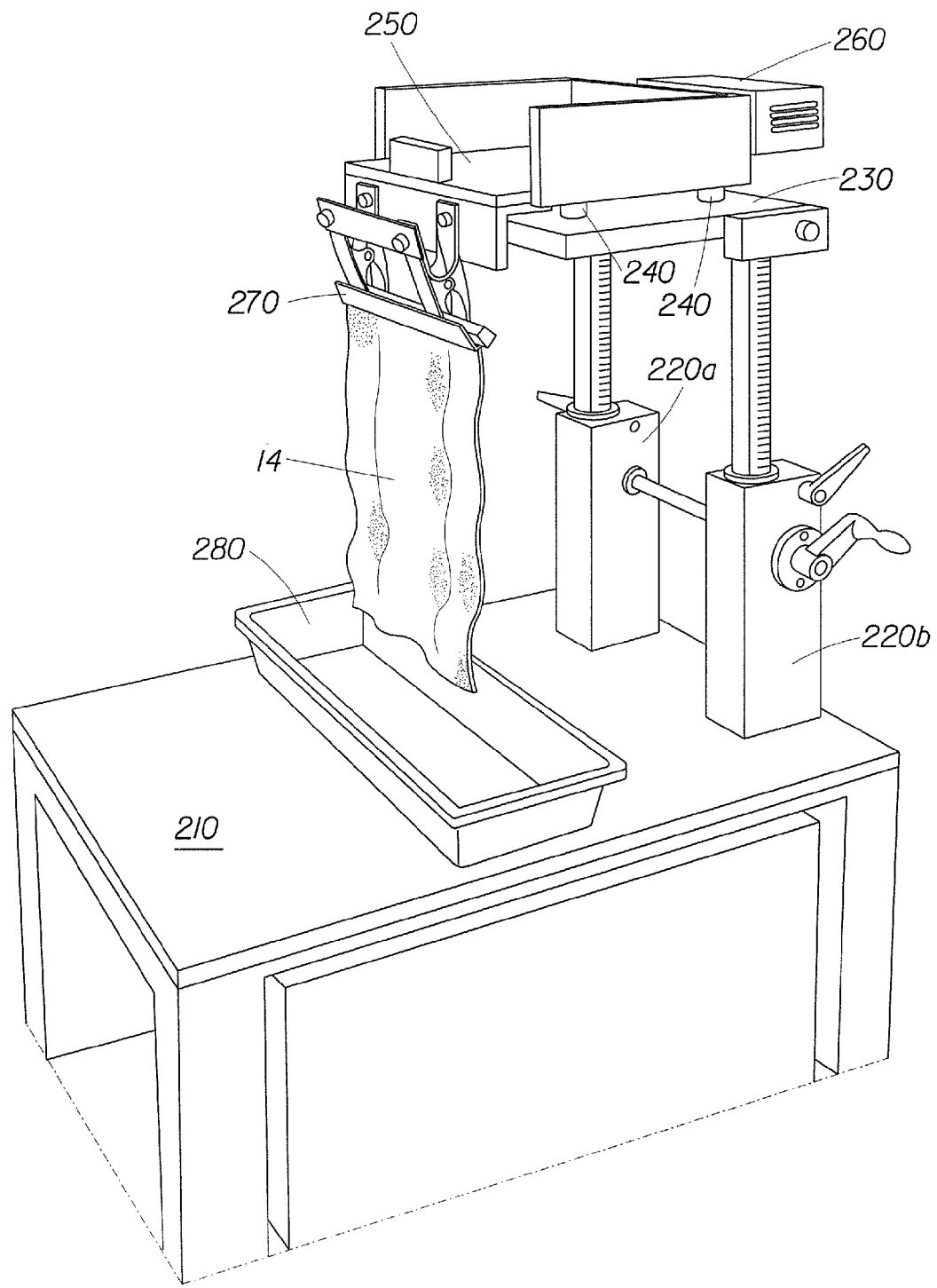
FIG. 15 is a perspective view of a "diaper shaker" for use in carrying out a wet immobilization test.

Turning to FIG. 11, portions of the first hopper 142, first support roll 140, and first printing roll 144 are illustrated. As also shown in FIG. 14, the first rotatable support roll 140, which has the same structure as the second rotatable support roll 152, comprises a rotatable drum 164 and a peripheral vented support grid 166 for receiving the first substrate 64.

Figure 12:
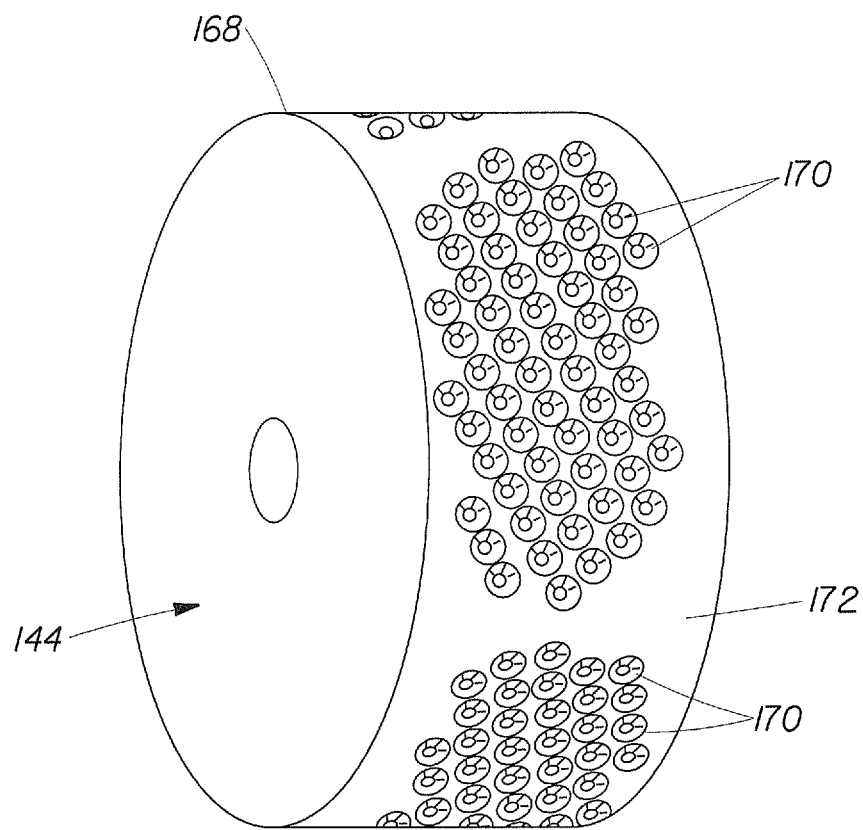
FIG. 12 is a perspective view of the printing roll illustrated in FIG. 11.
Figure 13:
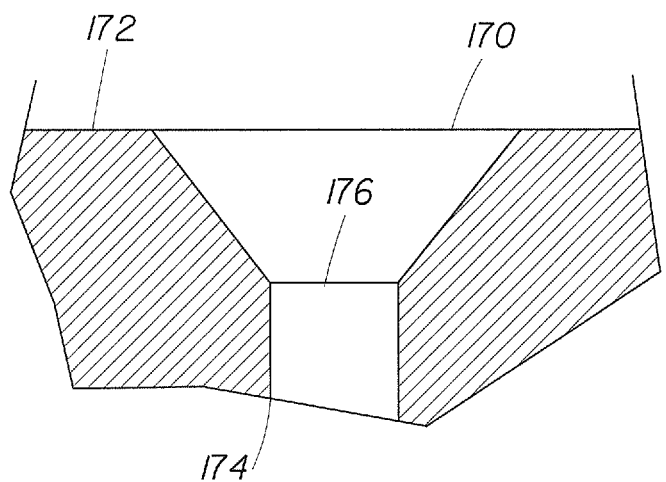
FIG. 13 is a partial sectional view of the printing roll illustrated in FIG. 12 showing an absorbent particulate polymer material reservoir.

As also illustrated in FIG. 12, the first printing roll 144, which has the same structure as the second printing roll 156, comprises a rotatable drum 168 and a plurality of absorbent particulate polymer material reservoirs 170 in a peripheral surface 172 of the drum 168. The reservoirs 170 best illustrated in FIG. 13, may have a variety of shapes, including cylindrical, conical, or any other shape. The reservoirs 170 may lead to an air passage 174 in the drum 168 and comprise a vented cover 176 for holding adhesive particulate polymer material 66 in the reservoir and preventing the adhesive particulate polymer material 66 from falling or being pulled into the air passage 174.

Figure 5:
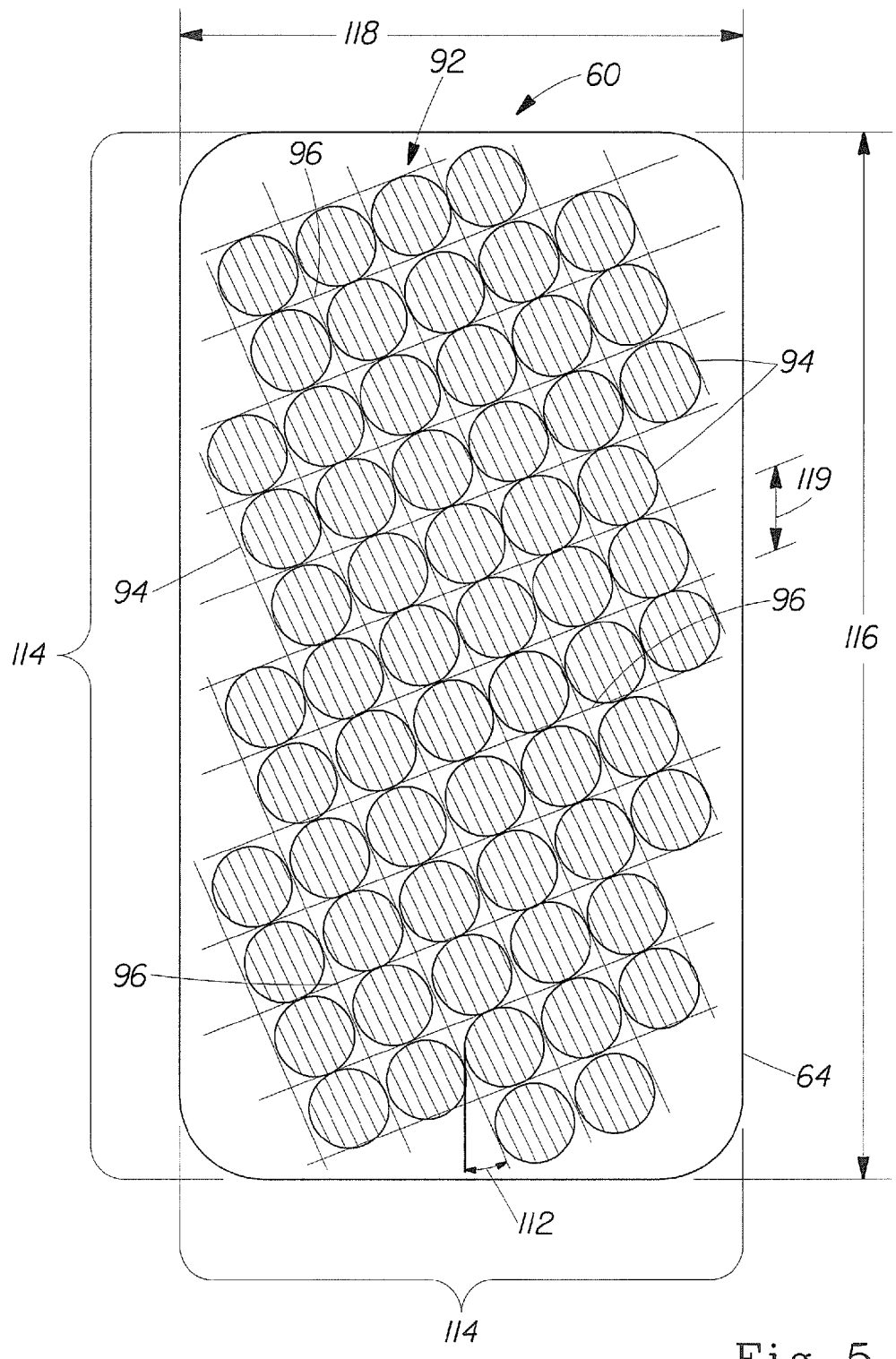
FIG. 5 is a plan view of the absorbent core layer illustrated in FIG. 3.
Figure 6:
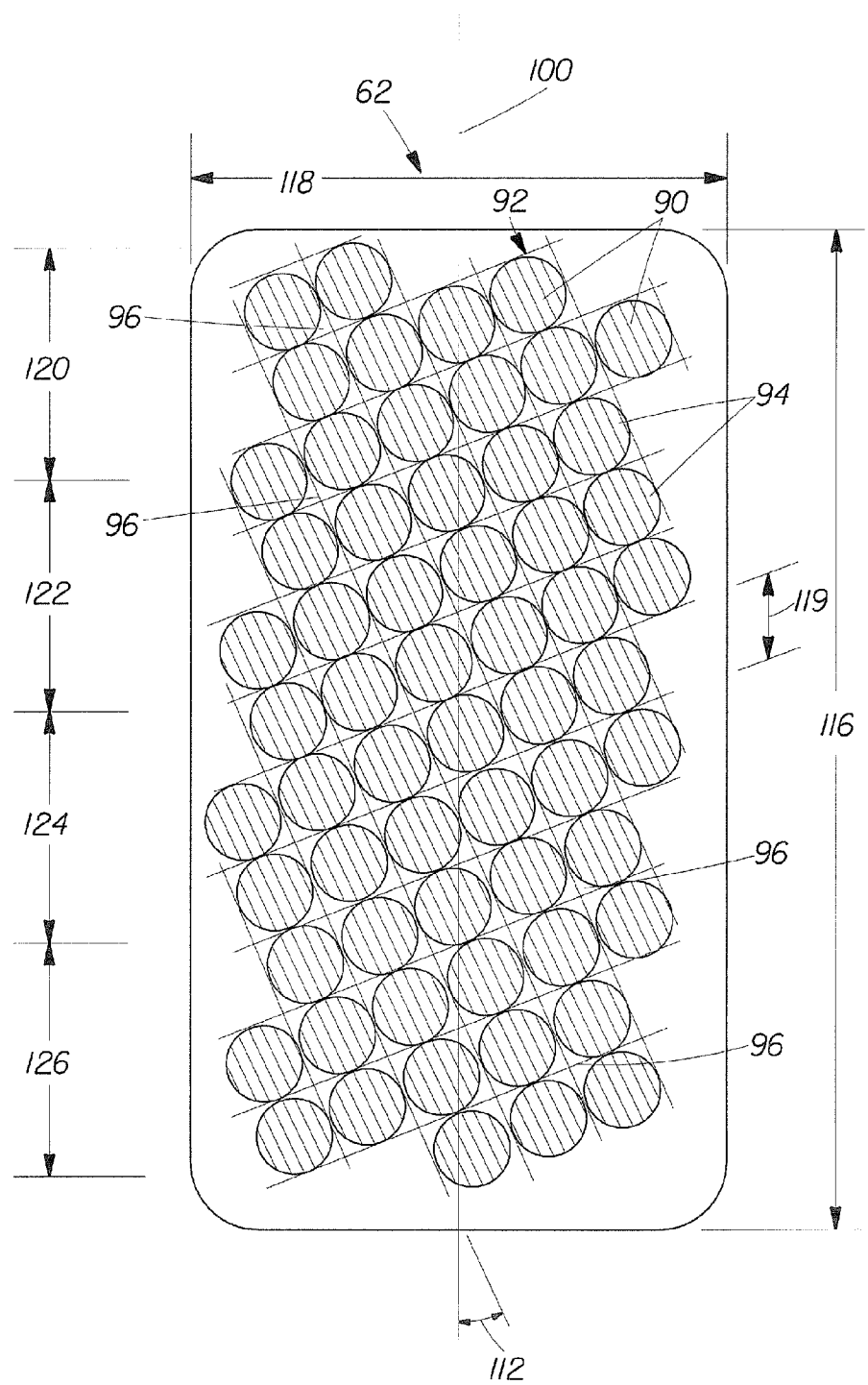
FIG. 6 is a plan view of a second absorbent core layer in accordance with an embodiment of this invention.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 5 and 6. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In an optional further process step a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

The test method and apparatuses described below may be useful in testing embodiments of this invention:

1. Wet Immobilization Test

Equipment
   Graduated Cylinder
   Stop watch (±0.1 sec)
   Scissors
   Light Box
   Pen
   Test solution: 0.90% saline solution at 37° C.
   Metal ruler traceable to NIST, DIN, JIS or other comparable National Standard
   PVC/metal dishes with a flat surface inside and a minimum length of the core bag length (n) to be measured and a maximum length n+30 mm, width of 105±5 mm, height of 30-80 mm or equivalent
   Electronic Force Gauge (Range 0 to 50 Kg)
   Wet Immobilization Impact Tester Equipment (WAIIT), Design package number: BM-00112.59500-R01 available from T.M.G. Technisches Buero Manfred Gruna Facilities:
   Standard laboratory conditions, temperature: 23° C.±2° C., relative humidity: <55%

Sample Preparation
1. Open the product, topsheet side up.
2. Unfold the diaper and cut the cuff elastics approximately every 2.5 cm to avoid chassis tension.
3. For pull-up products open the side seams and remove the waistbands.
4. Lay the core bag flat and rectangular topsheet side up onto the light box surface without any folds.
5. Switch on the light box to clearly identify the absorbent core outer edges.
6. With a ruler, draw a line at the front and back absorbent core outer edges.
7. Measure the distance (A), between the two markers and divide the value by 2, this will be calculated distance (B).
8. Measure the calculated distance (B) from front marker towards the middle of the core bag and mark it. At this marker draw a line in the cross direction.

Test Procedure

WAIIT Calibration:
1. Make sure that the sliding board is in the lower position. Open the front door of the WAIIT tester and connect the force gauge hook to the upper sample clamp of the WAIIT. Make sure that the clamp is closed before connecting the spring-balance.
2. Use both hands on the spring-balance to lift continuously and as slowly as possible up the sliding board towards the upper position. Record the average value ($m_1$) during the execution to the nearest 0.02 kg.
3. Guide down the sliding board as slowly as possible to the lower position and record the average value ($m_2$) read off during execution to the nearest 0.02 kg.
4. Calculate and report the delta of $m_1$-$m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:
  Drop height is 50 cm.
  Diaper load ($l_D$) is 73% of the core capacity (cc); $l_D$=0.73× cc.
  Core capacity (cc) is calculated as: cc=$m_{SAP}$×$SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test Execution:
1. Reset the balance to zero (tare), put the dry core bag on the balance, weigh and report it to the nearest 0.1 g.
2. Measure the appropriate volume Saline (0.9% NaCl in deionized water) with the graduated cylinder.
3. Lay the core bag, topsheet side up, flat into the PVC dish. Pour the saline evenly over the core bag.
4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (+/−1 minute) to allow all saline to be absorbed. Some drops may retain in the PVC dish. Use only the defined PVC/metal dish to guarantee homogenous liquid distribution and less retained liquid.
5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
6. Take the loaded core bag and cut the pad along the marked line in the cross direction.
7. Put the back of the wet core bag onto the balance ($m_1$). Weigh and report it to the nearest 0.1 g.
8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:
1. Record the dry core bag weight to the nearest 0.1 g.
2. Record the wet weight before ($m_{1\ front/back}$) and after ($m_{2\ front/back}$) testing, both to the nearest 0.1 g.
3. Calculate and report the average weight loss (Δm) to the nearest 0.1 g: $\Delta m=(m_{1front}+m_{1back})-(m_{2front}+m_{2back})$
4. Calculate and report the weight loss in percent to the nearest 1%, ($\Delta m_{rel}$): $\Delta m_{rel}=(((m_{1front}+m_{1back})-(m_{2front}+m_{2back}))\times 100)/(m_{1front}+m_{1back})$
5. Calculate and report Wet Immobilization (WI) as: WI=100%−$\Delta m_{rel}$ 2. Saline Flow Conductivity The method to determine the permeability of a swollen hydrogel layer 718 is the "Saline Flow Conductivity" also known as "Gel Layer Permeability" and is described in several references, including, EP A 640 330, filed on Dec. 1, 1993, U.S. Ser. No. 11/349,696, filed on Feb. 3, 2004, U.S. Ser. No. 11/347,406, filed on Feb. 3, 2006, U.S. Ser. No. 06/682,483, filed on Sep. 30, 1982, and U.S. Pat. No. 4,469,710, filed on Oct. 14, 1982. The equipment used for this method is described below.

Permeability Measurement System

Figure 16:
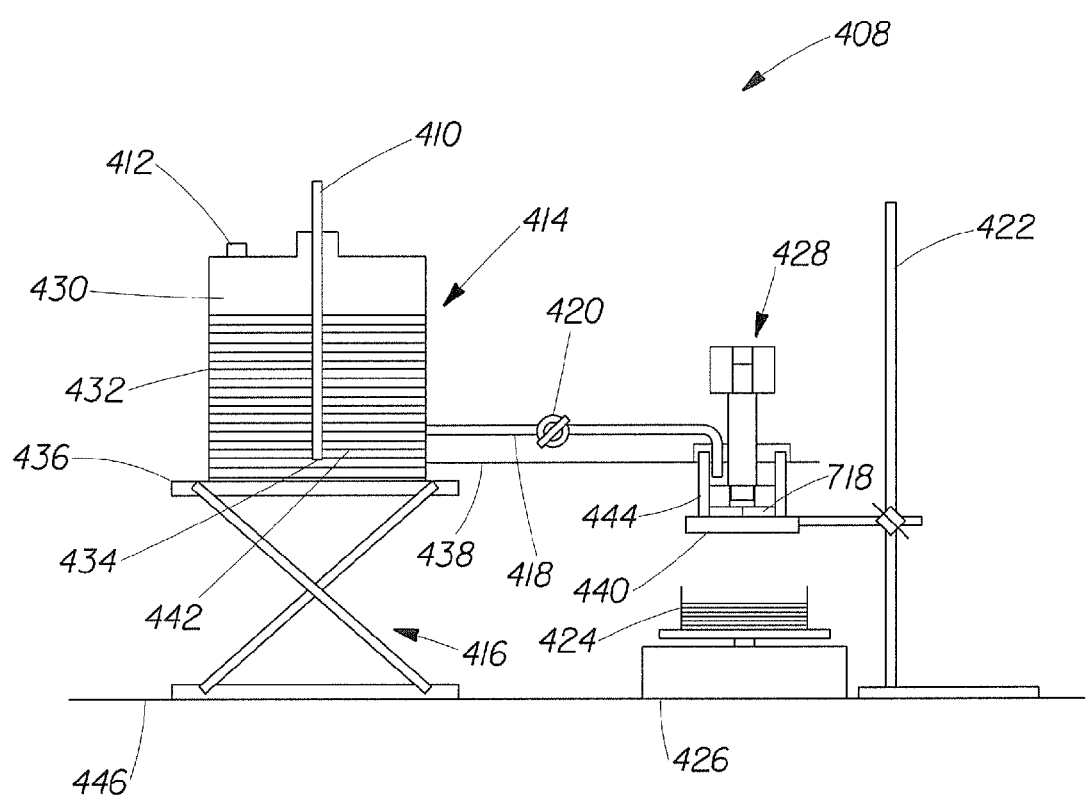
FIG. 16 is a partial cross-sectional side view of a suitable permeability measurement system for conducting the Saline Flow Conductivity Test.

FIG. 16 shows permeability measurement system 408 set-up with the constant hydrostatic head reservoir 414, open-ended tube for air admittance 410, stoppered vent for refilling 412, laboratory jack 416, delivery tube 418, stopcock 420, ring stand support 422, receiving vessel 424, balance 426 and piston/cylinder assembly 428.

Figure 17:
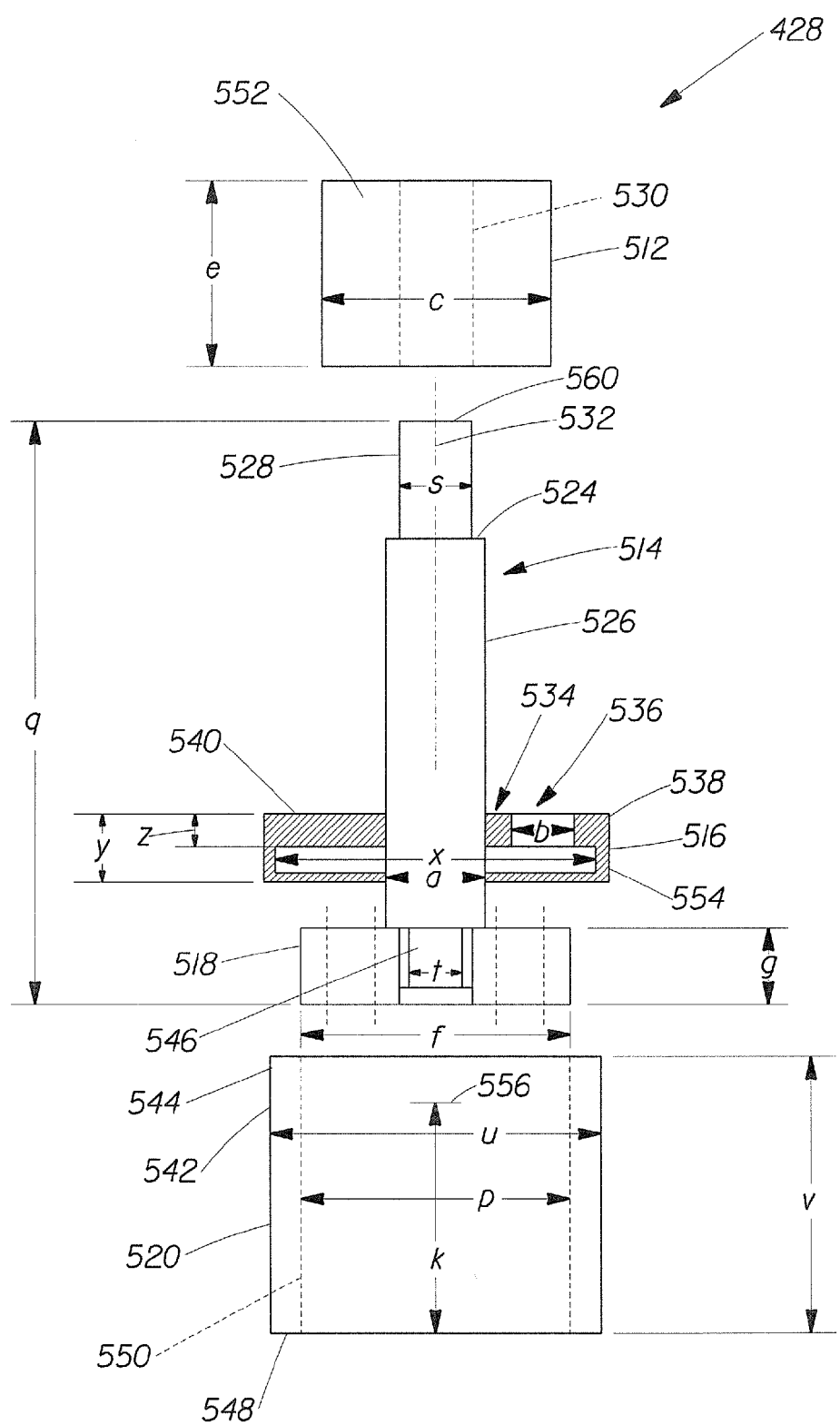
FIG. 17 is a cross-sectional side view of a piston/cylinder assembly for use in conducting the Saline Flow Conductivity Test.
Figure 18:
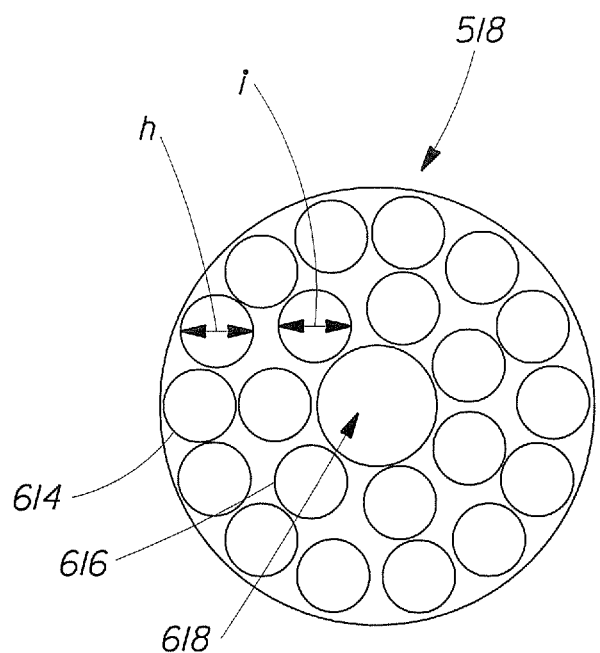
FIG. 18 is a top view of a piston head suitable for use in the piston/cylinder assembly shown in FIG. 17.

FIG. 17 shows the piston/cylinder assembly 428 comprising a metal weight 512, piston shaft 514, piston head 518, lid 516, and cylinder 520. The cylinder 520 is made of transparent polycarbonate (e.g., Lexan®) and has an inner diameter p of 6.00 cm (area=28.27 cm$^2$) with inner cylinder walls 550 which are smooth. The bottom 548 of the cylinder 520 is faced with a US. Standard 400 mesh stainless-steel screen cloth (not shown) that is bi-axially stretched to tautness prior to attachment to the bottom 548 of the cylinder 520. The piston shaft 514 is made of transparent polycarbonate (e.g., Lexan®) and has an overall length q of approximately 127 mm. A middle portion 526 of the piston shaft 514 has a diameter r of 21.15 mm. An upper portion 528 of the piston shaft 514 has a diameter s of 15.8 mm, forming a shoulder 524. A lower portion 546 of the piston shaft 514 has a diameter t of approximately 5/8 inch and is threaded to screw firmly into the center hole 618 (see FIG. 17) of the piston head 518. The piston head 518 is perforated, made of transparent polycarbonate (e.g., Lexan®), and is also screened with a stretched US. Standard 400 mesh stainless-steel screen cloth (not shown). The weight 512 is stainless steel, has a center bore 530, slides onto the upper portion 528 of piston shaft 514 and rests on the shoulder 524. The combined weight of the piston head 518, piston shaft 514 and weight 512 is 596 g (±6 g), which corresponds to 0.30 psi over the area of the cylinder 520. The combined weight may be adjusted by drilling a blind hole down a central axis 532 of the piston shaft 514 to remove material and/or provide a cavity to add weight. The cylinder lid 516 has a first lid opening 534 in its center for vertically aligning the piston shaft 514 and a second lid opening 536 near the edge 538 for introducing fluid from the constant hydrostatic head reservoir 414 into the cylinder 520.

A first linear index mark (not shown) is scribed radially along the upper surface 552 of the weight 512, the first linear index mark being transverse to the central axis 532 of the piston shaft 514. A corresponding second linear index mark (not shown) is scribed radially along the top surface 560 of the piston shaft 514, the second linear index mark being transverse to the central axis 532 of the piston shaft 514. A corresponding third linear index mark (not shown) is scribed along the middle portion 526 of the piston shaft 514, the third linear index mark being parallel with the central axis 532 of the piston shaft 514. A corresponding fourth linear index mark (not shown) is scribed radially along the upper surface 540 of the cylinder lid 516, the fourth linear index mark being transverse to the central axis 532 of the piston shaft 514. Further, a corresponding fifth linear index mark (not shown) is scribed along a lip 554 of the cylinder lid 516, the fifth linear index mark being parallel with the central axis 532 of the piston shaft 514. A corresponding sixth linear index mark (not shown) is scribed along the outer cylinder wall 542, the sixth linear index mark being parallel with the central axis 532 of the piston shaft 514. Alignment of the first, second, third, fourth, fifth, and sixth linear index marks allows for the weight 512, piston shaft 514, cylinder lid 516, and cylinder 520 to be re-positioned with the same orientation relative to one another for each measurement.

The cylinder 520 specification details are:
Outer diameter u of the Cylinder 520: 70.35 mm
Inner diameter p of the Cylinder 520: 60.0 mm
Height v of the Cylinder 520: 60.5 mm
The cylinder lid 516 specification details are:
Outer diameter w of cylinder lid 516: 76.05 mm
Inner diameter x of cylinder lid 516: 70.5 mm
Thickness y of cylinder lid 516 including lip 554: 12.7 mm
Thickness z of cylinder lid 516 without lip: 6.35 mm
Diameter a of first lid opening 534: 22.25 mm
Diameter b of second lid opening 536: 12.7 mm
Distance between centers of first and second lid openings 534 and 536: 23.5 mm
The weight 512 specification details are:
Outer diameter c: 50.0 mm
Diameter d of center bore 530: 16.0 mm
Height e: 39.0 mm
The piston head 518 specification details are
Diameter f: 59.7 mm
Height g: 16.5 mm
Outer holes 614 (14 total) with a 9.65 mm diameter h, outer holes 614 equally spaced with centers being 47.8 mm from the center of center hole 618
Inner holes 616 (7 total) with a 9.65 mm diameter i, inner holes 616 equally spaced with centers being 26.7 mm from the center of center hole 618
Center hole 618 has a diameter j of ⅝ inches and is threaded to accept a lower portion 546 of piston shaft 514.

Prior to use, the stainless steel screens (not shown) of the piston head 518 and cylinder 520 should be inspected for clogging, holes or over-stretching and replaced when necessary. An SFC apparatus with damaged screen can deliver erroneous SFC results, and must not be used until the screen has been replaced.

A 5.00 cm mark 556 is scribed on the cylinder 520 at a height k of 5.00 cm (±0.05 cm) above the screen (not shown) attached to the bottom 548 of the cylinder 520. This marks the fluid level to be maintained during the analysis. Maintenance of correct and constant fluid level (hydrostatic pressure) is critical for measurement accuracy.

A constant hydrostatic head reservoir 414 is used to deliver salt solution 432 to the cylinder 520 and to maintain the level of salt solution 432 at a height k of 5.00 cm above the screen (not shown) attached to the bottom 548 of the cylinder 520. The bottom 434 of the air-intake tube 410 is positioned so as to maintain the salt solution 432 level in the cylinder 520 at the required 5.00 cm height k during the measurement, i.e., bottom 434 of the air tube 410 is in approximately same plane 438 as the 5.00 cm mark 556 on the cylinder 520 as it sits on the support screen (not shown) on the ring stand 440 above the receiving vessel 424. Proper height alignment of the air-intake tube 410 and the 5.00 cm mark 556 on the cylinder 520 is critical to the analysis. A suitable reservoir 414 consists of a jar 430 containing: a horizontally oriented L-shaped delivery tube 418 for fluid delivery, a vertically oriented open-ended tube 410 for admitting air at a fixed height within the constant hydrostatic head reservoir 414, and a stoppered vent 412 for re-filling the constant hydrostatic head reservoir 414. Tube 410 has an internal diameter of xx mm. The delivery tube 418, positioned near the bottom 442 of the constant hydrostatic head reservoir 414, contains a stopcock 420 for starting/stopping the delivery of salt solution 432. The outlet 444 of the delivery tube 418 is dimensioned to be inserted through the second lid opening 536 in the cylinder lid 516, with its end positioned below the surface of the salt solution 432 in the cylinder 520 (after the 5.00 cm height of the salt solution 432 is attained in the cylinder 520). The air-intake tube 410 is held in place with an o-ring collar (not shown). The constant hydrostatic head reservoir 414 can be positioned on a laboratory jack 416 in order to adjust its height relative to that of the cylinder 520. The components of the constant hydrostatic head reservoir 414 are sized so as to rapidly fill the cylinder 520 to the required height (i.e., hydrostatic head) and maintain this height for the duration of the measurement. The constant hydrostatic head reservoir 414 must be capable of delivering salt solution 432 at a flow rate of at least 3 g/sec for at least 10 minutes.

The piston/cylinder assembly 428 is positioned on a 16 mesh rigid stainless steel support screen (not shown) (or equivalent) which is supported on a ring stand 440 or suitable alternative rigid stand. This support screen (not shown) is sufficiently permeable so as to not impede salt solution 432 flow and rigid enough to support the stainless steel mesh cloth (not shown) preventing stretching. The support screen (not shown) should be flat and level to avoid tilting the piston/cylinder assembly 428 during the test. The salt solution 432 passing through the support screen (not shown) is collected in a receiving vessel 424, positioned below (but not supporting) the support screen (not shown). The receiving vessel 424 is positioned on the balance 426 which is accurate to at least 0.01 g. The digital output of the balance 426 is connected to a computerized data acquisition system (not shown).

Preparation of Reagents (Not Illustrated)

Figure 19:
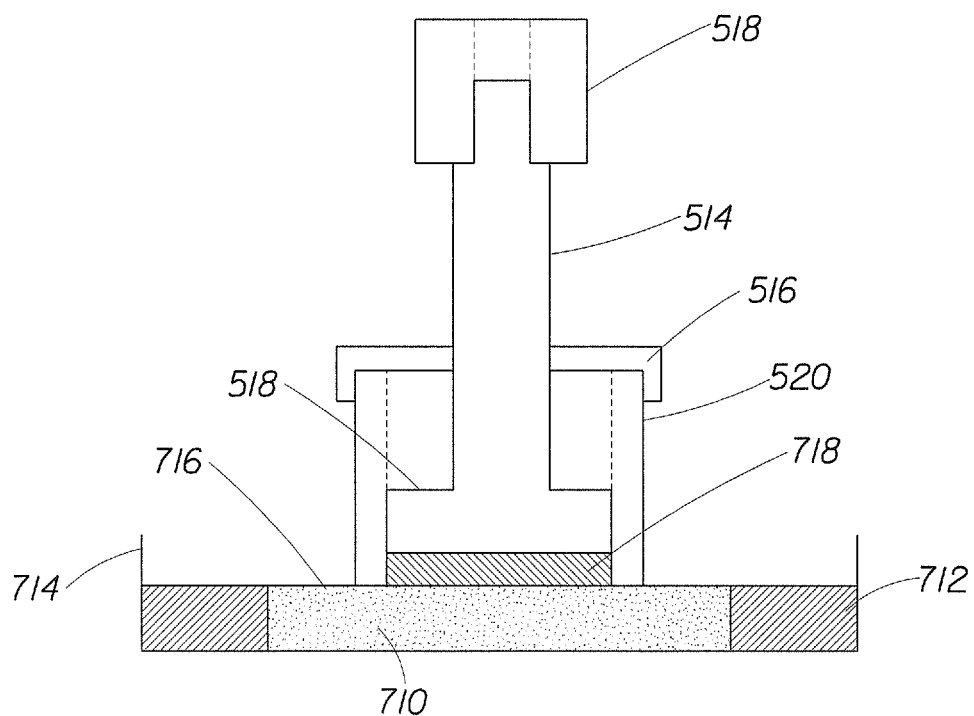
FIG. 19 is a cross-sectional side view of the piston/cylinder assembly of FIG. 17 placed on a fritted disc for the swelling phase.

Jayco Synthetic Urine (JSU) 712 (see FIG. 19) is used for a swelling phase (see SFC Procedure below) and 0.118 M Sodium Chloride (NaCl) Solution is used for a flow phase (see SFC Procedure below). The following preparations are referred to a standard 1 liter volume. For preparation of volumes other than 1 liter, all quantities are scaled accordingly.

JSU:

A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4)_2HPO_4$) 0.15 g
Calcium Chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution:

0.118 M Sodium Chloride is used as salt solution 432. Using a weighing paper or beaker 6.90 g (±0.01 g) of sodium chloride is weighed and quantitatively transferred into a 1L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 446. The piston/cylinder assembly 428 without superabsorbent is positioned under the caliper gauge (not shown) and a reading, $L_1$, is recorded to the nearest 0.01 mm.

The constant hydrostatic head reservoir 414 is filled with salt solution 432. The bottom 434 of the air-intake tube 410 is positioned so as to maintain the top part (not shown) of the liquid meniscus (not shown) in the cylinder 520 at the 5.00 cm mark 556 during the measurement. Proper height alignment of the air-intake tube 410 at the 5.00 cm mark 556 on the cylinder 520 is critical to the analysis.

The receiving vessel 424 is placed on the balance 426 and the digital output of the balance 426 is connected to a computerized data acquisition system (not shown). The ring stand 440 with a 16 mesh rigid stainless steel support screen (not shown) is positioned above the receiving vessel 424. The 16 mesh screen (not shown) should be sufficiently rigid to support the piston/cylinder assembly 428 during the measurement. The support screen (not shown) must be flat and level.

SFC Procedure 0.9 g (±0.05 g) of superabsorbent is weighed onto a suitable weighing paper using an analytical balance. 0.9 g (±0.05 g) of superabsorbent is weighed onto a suitable weighing paper using an analytical balance. The moisture content of the superabsorbent is measured according to the Edana Moisture Content Test Method 430.1-99 ("Superabsorbent materials-Polyacrylate superabsorbent powders-MOISTURE CONTENT-WEIGHT LOSS UPON HEATING" (February 99)). If the moisture content of the polymer is greater than 5%, then the polymer weight should be corrected for moisture (i.e., the added polymer should be 0.9 g on a dry-weight basis).

The empty cylinder 520 is placed on a level benchtop 446 and the superabsorbent is quantitatively transferred into the cylinder 520. The superabsorbent particles are evenly dispersed on the screen (not shown) attached to the bottom 548 of the cylinder 520 by gently shaking, rotating, and/or tapping the cylinder 520. It is important to have an even distribution of particles on the screen (not shown) attached to the bottom 548 of the cylinder 520 to obtain the highest precision result. After the superabsorbent has been evenly distributed on the screen (not shown) attached to the bottom 548 of the cylinder 520 particles must not adhere to the inner cylinder walls 550. The piston shaft 514 is inserted through the first lid opening 534, with the lip 554 of the lid 516 facing towards the piston head 518. The piston head 518 is carefully inserted into the cylinder 520 to a depth of a few centimeters. The lid 516 is then placed onto the upper rim 544 of the cylinder 520 while taking care to keep the piston head 518 away from the superabsorbent. The lid 516 and piston shaft 526 are then carefully rotated so as to align the third, fourth, fifth, and sixth linear index marks are then aligned. The piston head 518 (via the piston shaft 514) is then gently lowered to rest on the dry superabsorbent. The weight 512 is positioned on the upper portion 528 of the piston shaft 514 so that it rests on the shoulder 524 such that the first and second linear index marks are aligned. Proper seating of the lid 516 prevents binding and assures an even distribution of the weight on the hydrogel layer 718.

Swelling Phase:

An 8 cm diameter fritted disc (7 mm thick; e.g. Chemglass Inc. #CG 201-51, coarse porosity) 710 is saturated by adding excess JSU 712 to the fritted disc 710 until the fritted disc 710 is saturated. The saturated fritted disc 710 is placed in a wide flat-bottomed Petri dish 714 and JSU 712 is added until it reaches the top surface 716 of the fritted disc 710. The JSU height must not exceed the height of the fitted disc 710.

The screen (not shown) attached to the bottom 548 of the cylinder 520 is easily stretched. To prevent stretching, a sideways pressure is applied on the piston shaft 514, just above the lid 516, with the index finger while grasping the cylinder 520 of the piston/cylinder assembly 428. This "locks" the piston shaft 514 in place against the lid 516 so that the piston/cylinder assembly 428 can be lifted without undue force being exerted on the screen (not shown).

The entire piston/cylinder assembly 428 is lifted in this fashion and placed on the fritted disc 710 in the Petri dish 714. JSU 712 from the Petri dish 714 passes through the fritted disc 710 and is absorbed by the superabsorbent polymer (not shown) to form a hydrogel layer 718. The JSU 712 available in the Petri dish 714 should be enough for all the swelling phase. If needed, more JSU 712 may be added to the Petri dish 714 during the hydration period to keep the JSU 712 level at the top surface 716 of the fritted disc 710. After a period of 60 minutes, the piston/cylinder assembly 428 is removed from the fritted disc 710, taking care to lock the piston shaft 514 against the lid 516 as described above and ensure the hydrogel layer 718 does not lose JSU 712 or take in air during this procedure. The piston/cylinder assembly 428 is placed under the caliper gauge (not shown) and a reading, $L_2$, is recorded to the nearest 0.01 mm. If the reading changes with time, only the initial value is recorded. The thickness of the hydrogel layer 718, $L_0$ is determined from $L_2$-$L_1$ to the nearest 0.1 mm.

The entire piston/cylinder assembly 428 is lifted in this the fashion described above and placed on the support screen (not shown) attached to the ring stand 440. Care should be taken so that the hydrogel layer 718 does not lose JSU 712 or take in air during this procedure. The JSU 712 available in the Petri dish 714 should be enough for all the swelling phase. If needed, more JSU 712 may be added to the Petri dish 714 during the hydration period to keep the JSU 712 level at the 5.00 cm mark 556. After a period of 60 minutes, the piston/cylinder assembly 428 is removed, taking care to lock the piston shaft 514 against the lid 516 as described above. The piston/cylinder assembly 428 is placed under the caliper gauge (not shown) and the caliper (not shown) is measured as $L_2$ to the nearest 0.01 mm. The thickness of the hydrogel layer 718, $L_0$ is determined from $L_2$-$L_1$ to the nearest 0.1 mm. If the reading changes with time, only the initial value is recorded.

The piston/cylinder assembly 428 is transferred to the support screen (not shown) attached to the ring support stand 440 taking care to lock the piston shaft 514 in place against the lid 516. The constant hydrostatic head reservoir 414 is positioned such that the delivery tube 418 is placed through the second lid opening 536. The measurement is initiated in the following sequence:

a) The stopcock 420 of the constant hydrostatic head reservoir 410 is opened to permit the salt solution 432 to reach the 5.00 cm mark 556 on the cylinder 520. This salt solution 432 level should be obtained within 10 seconds of opening the stopcock 420.

b) Once 5.00 cm of salt solution 432 is attained, the data collection program is initiated.

With the aid of a computer (not shown) attached to the balance 426, the quantity of salt solution 432 passing through the hydrogel layer 718 is recorded at intervals of 20 seconds for a time period of 10 minutes. At the end of 10 minutes, the stopcock 420 on the constant hydrostatic head reservoir 410 is closed. The piston/cylinder assembly 428 is removed immediately, placed under the caliper gauge (not shown) and a reading, $L_3$, is recorded to the nearest 0.01 mm. The final thickness of the hydrogel layer 718, $L_f$ is determined from $L_3$-$L_1$ to the nearest 0.1 mm, as described above. The percent change in thickness of the hydrogel layer 718 is determined from $(L_f/L_0) \times 100$. Generally the change in thickness of the hydrogel layer 718 is within about ±10%.

The data from 60 seconds to the end of the experiment are used in the SFC calculation. The data collected prior to 60 seconds are not included in the calculation. The flow rate $F_s$ (in g/s) is the slope of a linear least-squares fit to a graph of the weight of salt solution 432 collected (in grams) as a function of time (in seconds) from 60 seconds to 600 seconds.

In a separate measurement, the flow rate through the permeability measurement system 408 ($F_a$) is measured as described above, except that no hydrogel layer 718 is present. If $F_a$ is much greater than the flow rate through the permeability measurement system 408 when the hydrogel layer 718 is present, $F_s$, then no correction for the flow resistance of the permeability measurement system 408 (including the piston/cylinder assembly 428) is necessary. In this limit, $F_g = F_s$, where $F_g$ is the contribution of the hydrogel layer 718 to the flow rate of the permeability measurement system 408. However if this requirement is not satisfied, then the following correction is used to calculate the value of $F_g$ from the values of $F_s$ and $F_a$:

$$F_g = (F_a \times F_s)/(F_a - F_s)$$

The Saline Flow Conductivity (K) of the hydrogel layer 718 is calculated using the following equation:

$$K = [F_g(t=0) \times L_0]/[\rho \times A \times \Delta P],$$

where $F_g$ is the flow rate in g/sec determined from regression analysis of the flow rate results and any correction due to permeability measurement system 408 flow resistance, $L_0$ is the initial thickness of the hydrogel layer 718 in cm, $\rho$ is the density of the salt solution 432 in gm/cm³. A (from the equation above) is the area of the hydrogel layer 718 in cm², $\Delta P$ is the hydrostatic pressure in dyne/cm², and the saline flow conductivity, K, is in units of cm³ sec/gm. The average of three determinations should be reported.

For hydrogel layers 718 where the flow rate is substantially constant, a permeability coefficient ($\kappa$) can be calculated from the saline flow conductivity using the following equation:

$$\kappa = K\eta$$

where $\eta$ is the viscosity of the salt solution 432 in poise and the permeability coefficient, $\kappa$, is in units of cm².

In general, flow rate need not be constant. The time-dependent flow rate through the system, $F_s(t)$ is determined, in units of g/sec, by dividing the incremental weight of salt solution 432 passing through the permeability measurement system 408 (in grams) by incremental time (in seconds). Only data collected for times between 60 seconds and 10 minutes is used for flow rate calculations. Flow rate results between 60 seconds and 10 minutes are used to calculate a value for $F_s$ (t=0), the initial flow rate through the hydrogel layer 718. $F_s$ (t=0) is calculated by extrapolating the results of a least-squares fit of $F_s(t)$ versus time to t=0.

3. Centrifuge Retention Capacity (CRC)

For most hydrogel-forming absorbent polymers, gel volume as a measurement of absorbent capacity is determined by the method described in U.S. Reissue Pat. No. 32,649 (Brandt et al), reissued Apr. 19, 1988 but using 0.9% saline solution instead of synthetic urine. The gel volume as well as the CRC capacity is calculated on a dry-weight basis. This method is to be used for all hydrogel-forming absorbent polymers which do not absorb Blue Dextran.

The method for measuring gel volume to be used for SAPs that absorb Blue Dextran (see gel volume method in U.S. Re Pat. No. 32,649) to the surfaces of the formed hydrogel (e.g., polymers prepared from cationic monomers), is as follows: For these hydrogel-forming polymers, the Absorptive Capacity test is used, but the dry weight of the hydrogel-forming polymer is used in the calculation instead of the as-is weight. See e.g., U.S. Pat. No. 5,124,188 (Roe et al), issued Jun. 23, 1992 at Columns 27-28 for description of the Absorptive Capacity test.

For the evaluation of the centrifuge retention capacity it has been found that the so-called tea-bag-evaluation or measurement (hereinafter CRC measurement) is most appropriate to reflect the maintenance of capillary pressure at situations approaching saturation of the absorbent capability of a SAP material. For the test standard laboratory conditions (21-23° C., 50% relative humidity) are used. Sample SAP material is kept dry in a tightly closing flask or other container, which is only opened upon start of the evaluation. Other material used in the evaluation (tissues, equipment etc.) is conditioned for 24 hours prior to measurements at the above laboratory conditions.

For the CRC measurement 0.2+/−0.0050 g of SAP particles are put into a tea bag (the bag needs to be freely liquid pervious and must retain the particles, i.e., the tea bag pores need to be not larger than the smallest particles. The tea bag should have a size of 60 mm×85 mm and is sealed by welding after filling. The tea bag is then immersed for 30 minutes in a 0.9% saline solution such that there is at least 0.83 l of solution per gram of SAP; there may be a substantial excess of this ratio. After the 30 minute immersion the tea bag is centrifuged at 250 g for 3 minutes to remove excess saline solution. The bag is weight to the nearest 0.01 g and the absorbed liquid is calculated. The result is reported by using the amount of dry SAP, which was put into the tea bag, as grams absorbed per gram of SAP particles.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a chassis including a topsheet and a backsheet; and
a substantially cellulose free absorbent core located between the topsheet and the backsheet and including first and second absorbent layers, the first absorbent layer including a first substrate and the second absorbent layer including a second substrate, the first and second absorbent layers further including absorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first absorbent layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area;
wherein the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such that the respective patterns of absorbent particulate polymer material are offset from one another;
wherein the width of the junction areas is less than about 5 mm,
wherein the absorbent particulate polymer material has a saline flow conductivity greater than about $100 \times 10^{-7}$ cm$^3 \cdot$sec/g and a centrifuge retention capacity of greater than about 20 g/g.

2. The disposable absorbent article of claim 1, wherein:
the absorbent particulate polymer material is deposited on the first and second substrates in respective patterns of land areas and junction areas between the land areas such that the absorbent particulate polymer material is discontinuously distributed on the first and second substrates; and
the first and second absorbent layers are combined together such the respective patterns of absorbent particulate polymer material are offset from one another.

3. The disposable absorbent article of claim 2, wherein the respective patterns are substantially the same.

4. The disposable absorbent article of claim 2, wherein the respective patterns are different.

5. The disposable absorbent article of claim 2, wherein the absorbent core has a front end and a rear end and a longitudinal axis extending from the rear end to the front end and the land areas of the respective patterns are arranged in a grid which is positioned at an angle from about 5 to about 85 degrees from the longitudinal axis of the absorbent core.

6. The disposable absorbent article of claim 2, wherein the absorbent core has a length extending front a rear end to a front end, and a width extending from a first edge to a second edge and perpendicularly to the length, and the respective patterns are offset from one another in both a direction parallel to the length and a direction parallel to the width.

7. The disposable absorbent article of claim 1, wherein the absorbent particulate polymer material area extends substantially entirely across the absorbent core.

8. The disposable absorbent article of claim 1, wherein the absorbent particulate polymer material area extends substantially entirely from front to back of the absorbent core.

9. The disposable absorbent article of claim 1, wherein the absorbent core consists essentially of the first and second substrates, the absorbent particulate polymer material, and the thermoplastic adhesive material.

10. The disposable absorbent article of claim 1, wherein the backsheet has a water vapor transmission rate of greater than about 3000 g/24 h/m$^2$ according to the test described herein.

11. The disposable absorbent article of claim 1 having an absorbent particulate polymer material loss of no more than about 70% according to the Wet Immobilization Test herein.

12. The disposable absorbent article of claim 1, wherein the absorbent particulate polymer material is present in the absorbent core in an amount greater than about 80% by weight of the absorbent core.

13. The disposable absorbent article of claim 1, wherein the absorbent core has a front end and a rear end and a longitudinal axis extending from the rear end to the front end and a plurality of absorbent zones, each of the plurality of absorbent zones having absorbent particulate polymer material present in differing amounts.

14. The disposable absorbent article of claim 13, wherein there is a gradual transition in amount of absorbent particulate polymer material form one of the plurality of absorbent zones to another.

15. The disposable absorbent article of claim 1, wherein the absorbent article is a diaper comprising a re-closable fastening system joined to the chassis for securing the diaper to a wearer.

16. The disposable absorbent article of claim 1, wherein the absorbent article is a pant-type diaper comprising at least two side panels joined to the chassis and to each other to form a pant.

17. The disposable absorbent article of claim 1, wherein the absorbent particulate polymer material has a saline flow conductivity greater than about $70 \times 10^{-7}$ cm$^3 \cdot$sec/g and a centrifuge retention capacity of greater than about 25 g/g.

18. An absorbent core comprising first and second absorbent layers, the first absorbent layer including a first substrate and the second absorbent layer including a second substrate, the first and second absorbent layers further including absorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first absorbent layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area, wherein the absorbent core is substantially cellulose free;
wherein the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such that the respective patterns of absorbent particulate polymer material are offset from one another;

wherein the width of the junction areas is less than about 5 mm, wherein the absorbent particulate polymer material has a saline flow conductivity greater than about $100 \times 10^{-7}$ cm$^3 \cdot$sec/g and a centrifuge retention capacity of greater than about 20 g/g.

19. The absorbent core of claim 18, wherein:

the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such the respective patterns of absorbent particulate polymer material are offset from one another.

20. The absorbent core of claim 18, wherein the absorbent particulate polymer material has a saline flow conductivity greater than about $70 \times 10^{-7}$ cm$^3 \cdot$sec/g and a centrifuge retention capacity of greater than about 25 g/g.

* * * * *